United States Patent
Bonn et al.

(10) Patent No.: US 9,877,332 B1
(45) Date of Patent: Jan. 23, 2018

(54) QUALITY OF SERVICE LEVEL BASED ON MEDICAL DATA FOR A WIRELESS COMMUNICATION DEVICE

(71) Applicant: Sprint Communications Company L.P., Overland Park, KS (US)

(72) Inventors: Mark J. Bonn, Granite Bay, CA (US); Abdolreza Asghari, Santa Clara, CA (US); James D. Kirby, San Mateo, CA (US); Dominick Mangiardi, Fremont, CA (US); John Tayag Susbilla, Milpitas, CA (US)

(73) Assignee: Sprint Communications Company L.P., Overland Park, KS (US)

( * ) Notice: Subject to any disclaimer, the term of this patent is extended or adjusted under 35 U.S.C. 154(b) by 42 days.

(21) Appl. No.: 14/863,023

(22) Filed: Sep. 23, 2015

(51) Int. Cl.
| | |
|---|---|
| *H04W 72/00* | (2009.01) |
| *H04W 72/10* | (2009.01) |
| *H04W 28/02* | (2009.01) |
| *G06F 19/00* | (2011.01) |
| *H04W 72/08* | (2009.01) |
| *H04W 88/08* | (2009.01) |

(52) U.S. Cl.
CPC ........ *H04W 72/10* (2013.01); *G06F 19/3418* (2013.01); *H04W 28/0215* (2013.01); *H04W 28/0268* (2013.01); *H04W 72/087* (2013.01); *H04W 88/08* (2013.01)

(58) Field of Classification Search
CPC ............. H04W 72/10; H04W 28/0215; H04W 72/087; H04W 28/0268; H04W 88/08; H04W 4/02; G06F 19/3418; A63B 2220/00; A63B 2220/80; A63B 2220/833; A63B 2220/836; A61B 5/0024
USPC ................ 455/410–411, 414.1–414.4, 452.2, 455/456.1–457, 550.1, 575.2, 576.6; 382/115
See application file for complete search history.

(56) References Cited

U.S. PATENT DOCUMENTS

| | | |
|---|---|---|
| 6,654,631 B1 | 11/2003 | Sahai |
| 8,489,066 B2 | 7/2013 | Imming et al. |
| 8,612,693 B2 | 12/2013 | Woods et al. |
| 8,630,820 B2 | 1/2014 | Amis |
| 8,634,799 B1 | 1/2014 | Economy et al. |
| 8,721,543 B2 | 5/2014 | Saffarian |
| 9,026,190 B2 | 5/2015 | Shenasa et al. |
| 9,035,775 B2 | 5/2015 | Margon |
| 2007/0047478 A1 | 3/2007 | Balachandran et al. |
| 2007/0103292 A1 | 5/2007 | Burkley et al. |
| 2011/0189971 A1 | 8/2011 | Faccin et al. |
| 2012/0082036 A1* | 4/2012 | Abedi ............... G06F 19/3418 370/241 |

(Continued)

*Primary Examiner* — Marcus Hammonds

(57) ABSTRACT

A wireless access node to facilitate increased quality of service in consideration of medical information comprises a wireless communication transceiver and a processing system. The wireless communication transceiver is configured to receive medical data transmitted from a wireless communication device served by the wireless access node, wherein the wireless communication device senses the medical data from a user of the wireless communication device. The processing system is configured to determine a quality of service level for the wireless communication device based on the medical data, and implement the quality of service level for the wireless communication device.

20 Claims, 5 Drawing Sheets

(56) References Cited

U.S. PATENT DOCUMENTS

| | | | |
|---|---|---|---|
| 2012/0092155 A1* | 4/2012 | Abedi | H04W 74/0875 340/539.12 |
| 2013/0109946 A1 | 5/2013 | Shim et al. | |
| 2013/0136036 A1* | 5/2013 | Chen | H04W 28/24 370/260 |
| 2016/0066279 A1* | 3/2016 | Lee | H04W 52/0261 370/311 |

* cited by examiner

QUALITY OF SERVICE LEVEL BASED ON MEDICAL DATA FOR A WIRELESS COMMUNICATION DEVICE

TECHNICAL BACKGROUND

Wireless communication devices transmit and receive information wirelessly via a wireless access node to communicate over a communication network. Typically, the wireless access node is part of a radio access network (RAN) which provides the wireless communication devices with access to further communication networks, systems, and devices. The wireless communication devices typically utilize "forward link" or "downlink" communication channels to receive voice and/or data transmitted from the wireless access node, and "reverse link" or "uplink" communication channels to transmit information up to the node.

In fourth generation (4G) long term evolution (LTE) communication systems, a wireless communication device is referred to as user equipment (UE), while a wireless access node is called an enhanced node B (eNodeB). Some eNodeBs utilize beamforming antennas, which steer the main beam of the antenna to momentarily cover specific geographic areas, typically at the edge of a cell sector. A beamforming antenna operates by manipulating phase differences of the outgoing signal on the antenna's elements, thereby creating a traffic beam which provides optimal coverage to one or more UE devices. Other advanced techniques may also be employed by an eNodeB to provide service to one or more UEs, such as various multiple-input multiple-output (MIMO) modes and configurations, quality of service class identifier (QCI) mechanisms to ensure bearer traffic is allocated the appropriate quality of service (QoS), and other methods.

Overview

A method of operating a communication system to facilitate increased quality of service in consideration of medical information is disclosed. The method comprises, in a wireless communication device, sensing medical data associated with a user of the wireless communication device, and transferring the medical data for delivery to a wireless access node serving the wireless communication device. The method further comprises, in the wireless access node, receiving the medical data transmitted from the wireless communication device, determining a quality of service level for the wireless communication device based on the medical data, and implementing the quality of service level for the wireless communication device.

A computer apparatus to operate a wireless access node to facilitate increased quality of service in consideration of medical information comprises software instructions and at least one non-transitory computer-readable storage medium storing the software instructions. The software instructions are configured, when executed by the wireless access node, to direct the wireless access node to receive medical data transmitted from a wireless communication device served by the wireless access node, wherein the wireless communication device senses the medical data from a user of the wireless communication device. The software instructions are further configured to direct the wireless access node to determine a quality of service level for the wireless communication device based on the medical data, and implement the quality of service level for the wireless communication device.

A wireless access node to facilitate increased quality of service in consideration of medical information comprises a wireless communication transceiver and a processing system. The wireless communication transceiver is configured to receive medical data transmitted from a wireless communication device served by the wireless access node, wherein the wireless communication device senses the medical data from a user of the wireless communication device. The processing system is configured to determine a quality of service level for the wireless communication device based on the medical data, and implement the quality of service level for the wireless communication device.

DETAILED DESCRIPTION

The following description and associated drawings teach the best mode of the invention. For the purpose of teaching inventive principles, some conventional aspects of the best mode may be simplified or omitted. The following claims specify the scope of the invention. Some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
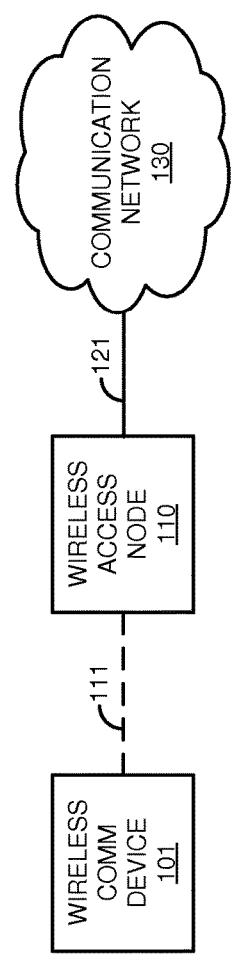
FIG. 1 is a block diagram that illustrates a communication system.

FIG. 1 is a block diagram that illustrates communication system 100. Communication system 100 includes wireless communication device 101, wireless access node 110, and communication network 130. Wireless communication device 101 and wireless access node 110 are in communication over wireless communication link 111. Wireless access node 110 and communication network 130 communicate over communication link 121.

Figure 2:
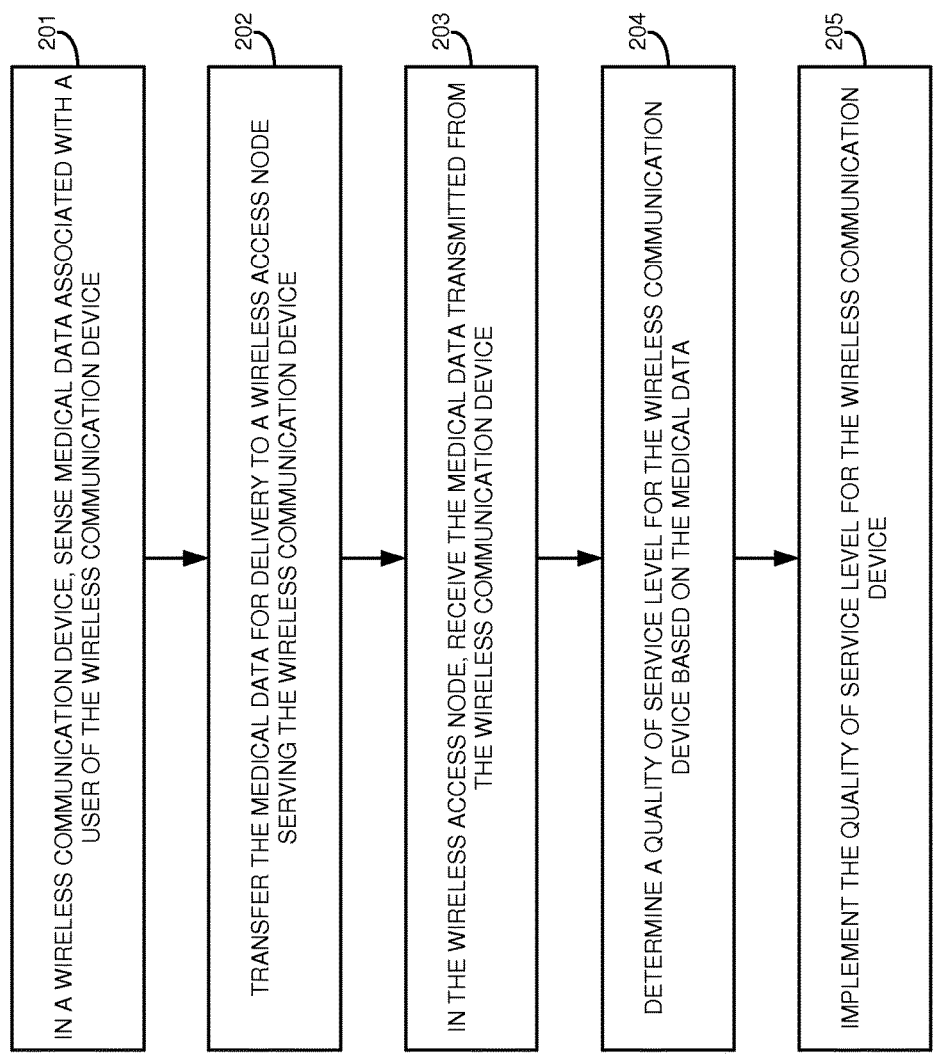
FIG. 2 is a flow diagram that illustrates an operation of the communication system.

FIG. 2 is a flow diagram that illustrates an operation of communication system 100. The steps of the operation are indicated below parenthetically. The operation of communication system 100 shown in FIG. 2 may be employed to facilitate increased quality of service in consideration of medical information.

As shown in the operational flow of FIG. 2, wireless communication device 101 senses medical data associated with a user of wireless communication device 101 (201). Typically, wireless communication device 101 utilizes built-in sensors and other equipment to sense the medical data associated with the user, although in some examples wireless communication device 101 could use external sensing equipment. For example, to sense the medical data, wireless communication device 101 could utilize electrocardiogram sensors, electrical heart activity sensors, heart rate monitors, perspiration sensors, retinal and ocular activity sensors, blood pressure monitors, blood sugar monitors, and any other medical sensing devices. In some examples, wireless communication device 101 could sense the medical data associated with the user of wireless communication device 101 by sensing electrical heart activity of the user to generate electrocardiogram data. Other medical data indicating a medical state of the user is possible and is included in the scope of this disclosure.

Wireless communication device 101 transfers the medical data for delivery to wireless access node 110 serving wireless communication device 101 (202). The medical data would typically be communicated to node 110 in bearer traffic or other messages in some examples. For example, the medical data could be carried in user plane messages over a data bearer service for delivery to wireless access node 110. In at least one implementation, a signaling priority could be based on the information received in the medical data. For example, medical thresholds could be used to signal priority requirements through non-access stratum (NAS) messages during radio resource control (RRC) configuration. In other words, RRC signaling messages would be used to establish the priority of the connection for wireless communication device 101. In this manner, wireless access node 110 could determine that the attachment request is high priority. Once wireless communication device 101 is attached with some high-priority cause, the default data bearer tunnel is created with high-priority quality of service (QoS) attributes and the medical data can be transferred on the bearer tunnel.

Wireless access node 110 receives the medical data transmitted from wireless communication device 101 (203). Wireless access node 110 would typically receive the medical data in bearer traffic exchanged between wireless communication device 101 and wireless access node 110 as described above, but node 110 could receive the medical data in other traffic or messages in some implementations.

Wireless access node 110 determines a quality of service level for wireless communication device 101 based on the medical data (204). The medical data typically dictates the level of quality of service that wireless access node 110 determines for the user's wireless communication device 101. Generally, the greater the severity of the medical condition indicated by the medical data, the higher the priority of the service request, resulting in a higher quality of the overall service level end-to-end in the network. For example, medical data indicating high stress or anxiety levels would result in a higher quality of service level than medical data indicating a calm and relaxed physical state of the user. The medical data could be compared to threshold values to determine whether the medical data indicates a medical condition that is severe enough to warrant an increase in quality of service for the user. In some examples, wireless access node 110 could determine the quality of service level for wireless communication device 101 based on the medical data by determining the quality of service level for wireless communication device 101 from a home subscriber server (HSS) profile associated with the user of wireless communication device 101. For example, the user's HSS profile could define one or more quality of service levels that the user has subscribed to or is authorized for depending on the medical data of the user. In some implementations, wireless access node 110 may first check the HSS profile of the user to verify that the user is authorized for a medically-elevated quality of service level before starting to monitor the medical data of the user to provide this service.

Wireless access node 110 implements the quality of service level for wireless communication device 101 (205). Typically, wireless access node 110 implements the quality of service level for wireless communication device 110 by increasing the quality of service level for device 101, which could be achieved in several ways. In some examples, wireless access node 110 implements the quality of service level for wireless communication device 101 by establishing a beamformed communication link with wireless communication device 101. Wireless access node 110 could also implement the quality of service level for wireless communication device 101 by selecting a multiple-input multiple-output (MIMO) mode for wireless communication device 101 optimized for redundancy. For example, wireless access node 110 could utilize MIMO to bring up more uplink and downlink antenna connections for more aggregated bandwidth in order to implement the quality of service level for wireless communication device 101. Additionally or alternatively, the quality of service level for wireless communication device 101 could be implemented by wireless access node 110 by applying priority scheduling for quality of service class identifier (QCI)-five traffic associated with wireless communication device 101. For example, the IP packet flow of wireless communication device 101 could be set to a higher priority, or a custom QCI value could be assigned for the priority service in some implementations. Combinations of these and other service-prioritizing techniques may be utilized by wireless access node 110 to implement a higher quality of service level for wireless communication device 101 and are within the scope of this disclosure.

Advantageously, wireless access node 110 can monitor medical data of a user of wireless communication device 101 to determine a quality of service level for wireless communication device 101 based on the medical data. Users who are older, have health problems, or are otherwise at risk for medical emergencies can subscribe to this service to help ensure that their communications receive priority treatment and handling from increased quality of service when their medical data indicates a medical state of concern. In addition, law enforcement officers, fire fighters, emergency medical technicians, and other first responders could have their medical information monitored and receive wireless priority services whenever their biometric data indicates their involvement in an emergency situation, such as a high or extreme stress condition with stress inducing impacts. This dynamic priority service assignment enables first responders and other users in emergency situations to receive the highest priority on the network which helps to avoid network blocks and dropped calls, service impacts due to congestion controls, and ensures voice call continuity during handovers.

Now referring back to FIG. 1, wireless communication device 101 comprises any device having wireless communication connectivity with hardware and circuitry programmed to function as a telecommunications device, such as Radio Frequency (RF) communication circuitry and an antenna. The RF communication circuitry typically includes an amplifier, filter, modulator, and signal processing circuitry. Wireless communication device 101 may also include a user interface, memory system, software, processing circuitry, or some other communication components. For example, wireless communication device 101 could comprise a telephone, transceiver, mobile phone, cellular phone, smartphone, computer, personal digital assistant (PDA), e-book, game console, mobile Internet device, wireless network interface card, media player, or some other wireless communication apparatus—including combinations thereof. Wireless network protocols that may be utilized by wireless communication device 101 include Code Division Multiple Access (CDMA) 1×RTT, Global System for Mobile communications (GSM), Universal Mobile Telecommunications System (UMTS), High-Speed Packet Access (HSPA), Evolution-Data Optimized (EV-DO), EV-DO rev. A, B, and C, Third Generation Partnership Project Long Term Evolution (3GPP LTE), LTE Advanced, Worldwide Interoperability for Microwave Access (WiMAX), IEEE 802.11 protocols (Wi-Fi), Bluetooth, Internet, telephony, or any other wireless network protocol that facilitates communication between wireless communication device 101 and wireless access node 110.

Wireless access node 110 comprises RF communication circuitry and an antenna. The RF communication circuitry typically includes an amplifier, filter, RF modulator, and signal processing circuitry. Wireless access node 110 may also comprise a router, server, memory device, software, processing circuitry, cabling, power supply, network communication interface, structural support, or some other communication apparatus. Wireless access node 110 could comprise a base station, Internet access node, telephony service node, wireless data access point, or some other wireless communication system—including combinations thereof. Some examples of wireless access node 110 include a base transceiver station (BTS), base station controller (BSC), radio base station (RBS), Node B, enhanced Node B (eNodeB), and others—including combinations thereof. Wireless network protocols that may be utilized by wireless access node 110 include CDMA, GSM, UMTS, HSPA, EV-DO, EV-DO rev. A, B, and C, 3GPP LTE, LTE Advanced, WiMAX, Wi-Fi, Bluetooth, Internet, telephony, or some other communication format—including combinations thereof.

Communication network 130 comprises the core network of a wireless communication service provider, and could include routers, gateways, telecommunication switches, servers, processing systems, or other communication equipment and systems for providing communication and data services. Communication network 130 could comprise wireless communication nodes, telephony switches, Internet routers, network gateways, computer systems, communication links, or some other type of communication equipment—including combinations thereof. Communication network 130 may also comprise optical networks, asynchronous transfer mode (ATM) networks, packet networks, radio access networks (RAN), local area networks (LAN), metropolitan area networks (MAN), wide area networks (WAN), or other network topologies, equipment, or systems—including combinations thereof. Communication network 130 may be configured to communicate over metallic, wireless, or optical links—including combinations thereof. Communication network 130 may be configured to use time-division multiplexing (TDM), Internet Protocol (IP), Ethernet, optical networking, wireless protocols, communication signaling, or some other communication format—including combinations thereof. In some examples, communication network 130 includes further access nodes and associated equipment for providing communication services to many wireless communication devices across a large geographic region.

Wireless communication link 111 use the air or space as the transport medium. Wireless communication link 111 may use various protocols, such as CDMA, GSM, UMTS, HSPA, EV-DO, EV-DO rev. A, B, and C, 3GPP LTE, LTE Advanced, WiMAX, Wi-Fi, Bluetooth, Internet, telephony, or some other communication format—including combinations thereof. Wireless communication link 111 may comprise many different signals sharing the same link. For example, \wireless communication link 111 could include multiple signals operating in a single propagation path comprising multiple communication sessions, frequencies, timeslots, transportation ports, logical transportation links, network sockets, IP sockets, packets, or communication directions—including combinations thereof.

Communication link 121 uses metal, air, space, optical fiber such as glass or plastic, or some other material as the transport medium—including combinations thereof. Communication link 121 could use various communication protocols, such as TDM, IP, Ethernet, telephony, optical networking, hybrid fiber coax (HFC), communication signaling, wireless protocols, or some other communication format—including combinations thereof. Communication link 121 may be a direct link or could include intermediate networks, systems, or devices.

Figure 3:
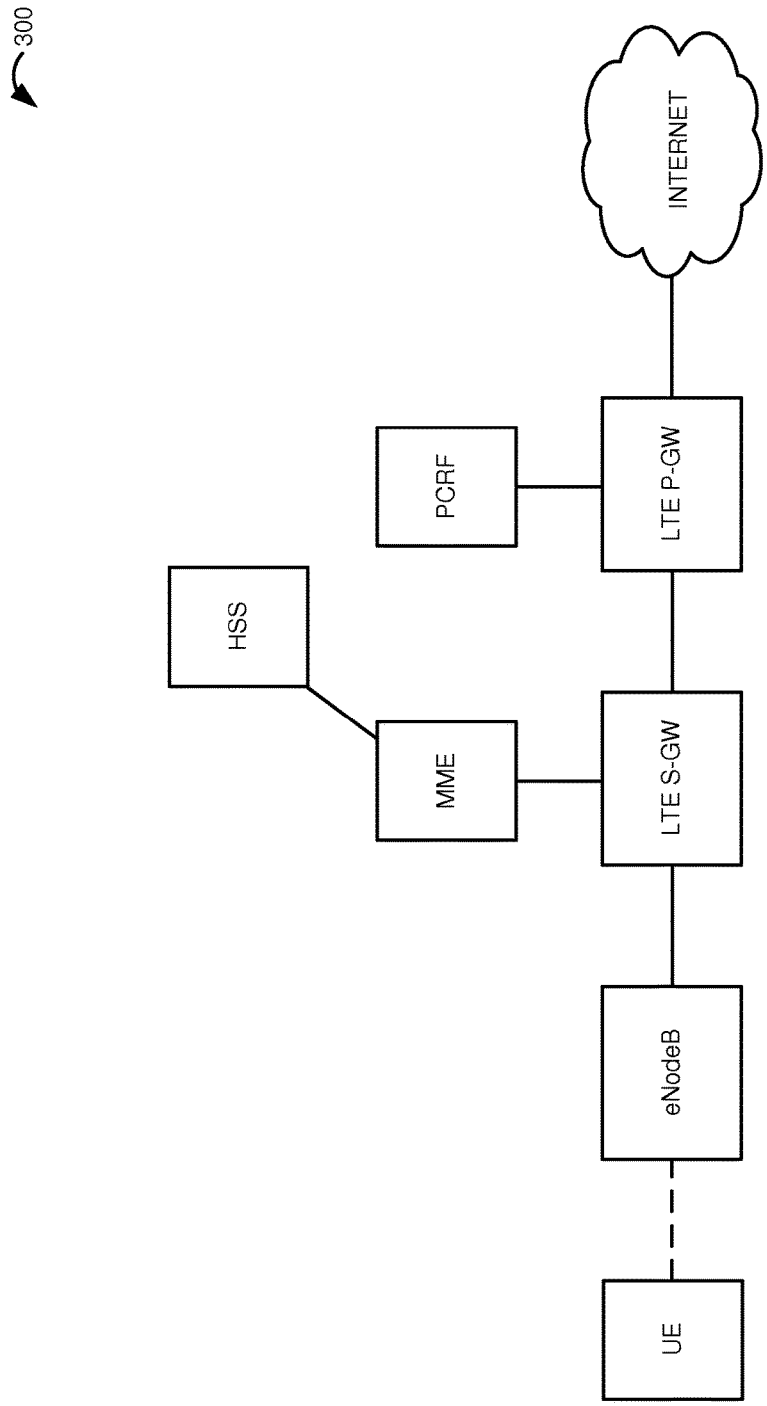
FIG. 3 is a block diagram that illustrates a communication system in an exemplary embodiment.

FIG. 3 is a block diagram that illustrates long term evolution (LTE) communication system 300 in an exemplary embodiment. LTE communication system 300 includes an enhanced Node B (eNodeB) base station that is in communication with network elements of the LTE communication network. The eNodeB base station provides an example of wireless access node 110, although node 110 may use alternative configurations. The LTE communication network in this example includes a mobility management entity (MME), serving gateway (S-GW), packet data network gateway (P-GW), home subscriber server (HSS), policy and charging rules function (PCRF), and other network elements typically found in a 4G LTE communication network that are not shown for clarity. LTE communication system 300 also includes a user equipment (UE) device. The UE provides an example of wireless communication device 101, although device 101 could use alternative configurations. In this example, the UE is shown as being served by the eNodeB, which has a wireless coverage area that is typically defined by the signal propagation characteristics and coverage capabilities of the eNodeB.

In operation, a user typically operates the UE to engage in an internet data session via the LTE access network. To establish a connection for the communication session, the eNodeB sends a resource allocation that specifies a resource block for the UE. The UE receives the resource allocation and sends a radio resource control (RRC) connection request message using the resource block allocated by the eNodeB. The UE includes an establishment clause in the RRC connection request which may identify the reason that the UE is requesting a connection. In some examples, the establishment clause could comprise an indication of an emergency call, high priority access, mobile terminating access, mobile originating signaling, mobile originating data, and others. Additionally or alternatively, such medical data could be included in non-access stratum (NAS) messages transferred by the UE to the eNodeB.

In this example, the user operating the UE has subscribed to a medical data monitoring service which increases the quality of service of the user's connection when the medical data indicates that the user is in a medical state or emergency situation. Specifically, the user has electrocardiogram (EKG) monitoring which provides a more reliable connection based on the user's heart activity. The UE operated by the user in this example includes electrical heart activity sensors which sense and determine EKG readings for the user. In some implementations, wireless RRC signaling messages transferred by the UE to the eNodeB could include a priority flag due to medical requirements, which would signal the eNodeB to establish priority services for the UE. The UE then attaches with priority and bearer services are created with priority. The actual EKG data could then be transmitted over the data bearer service normally, but the bearer would not be pre-emptable due to the QoS and address resolution protocol (ARP) used by the priority for the user.

The eNodeB verifies that the user is authorized for enhanced QoS based on medical data monitoring. The indication that the user is authorized for such service could be stored at the HSS, PCRF, or some other network element. In some examples, when the eNodeB receives a default bearer from the HSS or PCRF when establishing a communication session for the UE, there could be an indication that the user is authorized for enhanced QoS based on medical data monitoring included in the default bearer allocation. For example, when the P-GW requests a bearer for the UE, the PCRF could indicate that the user is authorized for EKG monitoring per connection. The P-GW cannot perform this service, so the P-GW would indicate to the eNodeB serving the UE to provide the EKG monitoring service. For priority services, the PCRF can override the attributes of the bearer to create a high-priority default data bearer. The MME signals the S-GW, which signals the P-GW, which signals the PCRF for any subscriber-specific priority override.

After the eNodeB receives the indication that the user should receive enhanced QoS based on monitoring the user's real-time medical data, the eNodeB receives indications of the medical state of the user transmitted by the UE, such as the user's heart rate, EKG readings, blood pressure, and other factors that indicate the user's stress level and health condition. If one or more of these factors exceed predetermined threshold values, the eNodeB implements enhanced QoS for the UE. For example, the eNodeB could increase the power of the communication channel provided to the UE using beamforming, which could provide increased range and a stronger wireless signal for the UE. Using beamforming, the eNodeB could direct more energy to the UE operated by the user that is exhibiting medical data indicative of a health condition or stressful situation which would help the signal reach the user and stay connected to the network. In another example, the eNodeB could implement enhanced QoS for the user responsive to the user's medical data by selecting a multiple-input multiple-output (MIMO) mode for the UE that is optimized for redundancy. The eNodeB could also prioritize certain QoS class identifier (QCI) traffic associated with the UE to provide enhanced QoS to the user. For example, the eNodeB could schedule QCI-5 traffic associated with the UE before other users who do not have medical data monitoring in order to implement the enhanced QoS for the UE based on the user's medical state. In this manner, the user would receive enhanced QoS and priority treatment dynamically based on monitoring the user's health and stress levels, thereby ensuring improved connection reliability, voice call continuity during handovers, and reduced service impacts due to congestion controls.

Figure 4:
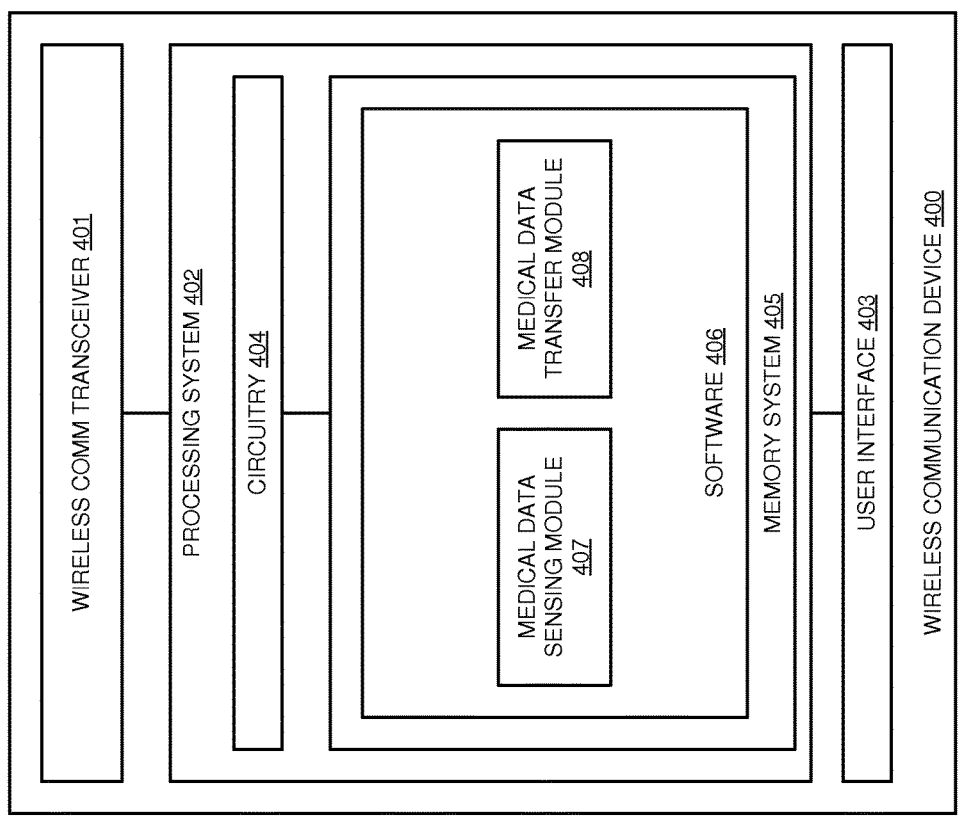
FIG. 4 is a block diagram that illustrates a wireless communication device.

FIG. 4 is a block diagram that illustrates wireless communication device 400. Wireless communication device 400 provides an example of wireless communication device 101, although device 101 could use alternative configurations. Wireless communication device 400 comprises wireless communication transceiver 401, processing system 402, and user interface 403. Processing system 402 is linked to wireless communication transceiver 401 and user interface 403. Processing system 402 includes processing circuitry 404 and memory system 405 that stores operating software 406. Operating software 406 comprises software modules 407 and 408. Wireless communication device 400 may include other well-known components such as a battery and enclosure that are not shown for clarity. Wireless communication device 400 may comprise a telephone, computer, e-book, mobile Internet appliance, media player, game console, wireless network interface card, or some other wireless communication apparatus—including combinations thereof.

Wireless communication transceiver 401 comprises RF communication circuitry and an antenna. The RF communication circuitry typically includes an amplifier, filter, RF modulator, and signal processing circuitry. Wireless communication transceiver 401 may also include a memory system, software, processing circuitry, or some other communication device. Wireless communication transceiver 401 may use various protocols, such as CDMA, GSM, UMTS, HSPA, EV-DO, EV-DO rev. A, 3GPP LTE, LTE Advanced, WiMAX, Wi-Fi, Bluetooth, Internet, telephony, or some other wireless communication format. Wireless communication transceiver 401 is configured to transfer medical data for delivery to a wireless access node serving wireless communication device 400.

User interface 403 comprises components that interact with a user to receive user inputs and to present media and/or information. User interface 403 may include a speaker, microphone, buttons, lights, display screen, touchscreen, touch pad, scroll wheel, communication port, or some other user input/output apparatus—including combinations thereof. User interface 403 may be omitted in some examples.

Processing circuitry 404 comprises microprocessor and other circuitry that retrieves and executes operating software 406 from memory system 405. Processing circuitry 404 may comprise a single device or could be distributed across multiple devices—including devices in different geographic areas. Processing circuitry 404 may be embedded in various types of equipment. Processing circuitry 404 is typically mounted on a circuit board that may also hold memory system 405 and portions of wireless communication transceiver 401 and user interface 403. Memory system 405 comprises a non-transitory computer readable storage medium, such as a disk drive, flash drive, data storage circuitry, or some other hardware memory apparatus. Memory system 405 may comprise a single device or could be distributed across multiple devices—including devices in different geographic areas. Memory system 405 may be embedded in various types of equipment. In some examples, a computer apparatus could comprise memory system 405 and operating software 406. Operating software 406 comprises computer programs, firmware, or some other form of machine-readable processing instructions. Operating software 406 may include an operating system, utilities, drivers, network interfaces, applications, or some other type of software. In this example, operating software 406 comprises software modules 407 and 408, although software 406 could have alternative configurations in other examples.

When executed by processing circuitry 404, operating software 406 directs processing system 402 to operate wireless communication device 400 as described herein for wireless communication device 101. In particular, operating software 406 directs processing system 402 to sense medical data associated with a user of wireless communication device 400. Operating software 406 further directs processing system 402 to direct wireless communication transceiver 401 to transfer the medical data for delivery to a wireless access node serving wireless communication device 400.

In this example, operating software 406 comprises a medical data sensing software module 407 that senses medical data associated with a user of wireless communication device 400. Additionally, operating software 406 comprises a medical data transfer software module 408 that transfers the medical data for delivery to a wireless access node serving wireless communication device 400.

Figure 5:
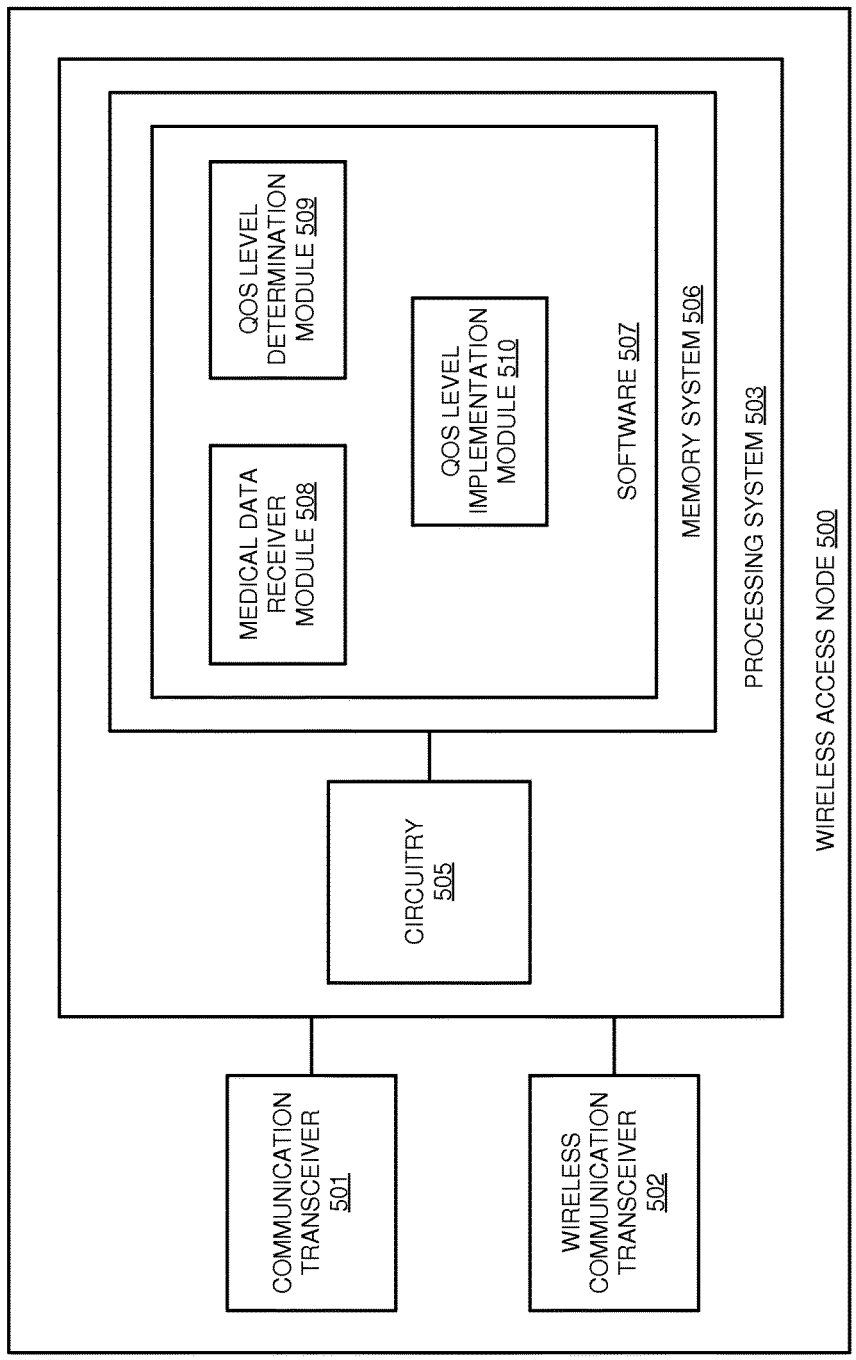
FIG. 5 is a block diagram that illustrates a wireless access node.

FIG. 5 is a block diagram that illustrates wireless access node 500. Wireless access node 500 provides an example of wireless access node 110, although node 110 may have alternative configurations. Wireless access node 500 comprises communication transceiver 501, wireless communication transceiver 502, and processing system 503. Processing system 503 is linked to communication transceiver 501 and wireless communication transceiver 502. Processing system 503 includes processing circuitry 505 and memory system 506 that stores operating software 507. Operating software 507 comprises software modules 508-510.

Communication transceiver 501 comprises components that communicate over communication links, such as network cards, ports, RF transceivers, processing circuitry and software, or some other communication components. Communication transceiver 501 may be configured to communicate over metallic, wireless, or optical links. Communication transceiver 501 may be configured to use TDM, IP, Ethernet, optical networking, wireless protocols, communication signaling, or some other communication format—including combinations thereof.

Wireless communication transceiver 502 comprises RF communication circuitry and an antenna. The RF communication circuitry typically includes an amplifier, filter, RF modulator, and signal processing circuitry. Wireless communication transceiver 502 may also include a memory system, software, processing circuitry, or some other communication device. Wireless communication transceiver 502 may use various protocols, such as CDMA, GSM, UMTS, HSPA, EV-DO, EV-DO rev. A, B, and C, 3GPP LTE, WiMAX, Wi-Fi, Bluetooth, Internet, telephony, or some other wireless communication format. Wireless communication transceiver 502 may be configured to receive medical data transmitted from a wireless communication device. Wireless communication transceiver 502 may also be configured to implement a quality of service level for the wireless communication device.

Processing circuitry 505 comprises microprocessor and other circuitry that retrieves and executes operating software 507 from memory system 506. Processing circuitry 505 may comprise a single device or could be distributed across multiple devices—including devices in different geographic areas. Processing circuitry 505 may be embedded in various types of equipment. Memory system 506 comprises a non-transitory computer readable storage medium, such as a disk drive, flash drive, data storage circuitry, or some other hardware memory apparatus. Memory system 506 may comprise a single device or could be distributed across multiple devices—including devices in different geographic areas. Memory system 506 may be embedded in various types of equipment. In some examples, a computer apparatus could comprise memory system 506 and operating software 507. Operating software 507 comprises computer programs, firmware, or some other form of machine-readable processing instructions. Operating software 507 may include an operating system, utilities, drivers, network interfaces, applications, or some other type of software. In this example, operating software 507 comprises software modules 508-510, although software 507 could have alternative configurations in other examples.

When executed by circuitry 505, operating software 507 directs processing system 503 to operate as described herein for wireless access node 110. In particular, operating software 507 may direct processing system 503 to direct wireless communication transceiver 502 to receive medical data transmitted from a wireless communication device. Operating software 507 further directs processing system 503 to determine a quality of service level for the wireless communication device based on the medical data. In addition, operating software 507 directs processing system 503 to implement the quality of service level for the wireless communication device.

In this example, operating software 507 comprises a medical data receiver software module 508 that receives medical data transmitted from a wireless communication device. Operating software 507 also comprises a QoS level determination software module 509 that determines a quality of service level for the wireless communication device based on the medical data. Operating software 507 further comprises a QoS level implementation software module 510 that implements the quality of service level for the wireless communication device.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A method of operating a long term evolution (LTE) communication system to facilitate increased quality of service in consideration of medical information, the method comprising:
   in a user equipment (UE), wirelessly transmitting a radio resource control (RRC) message comprising a priority flag for delivery to an LTE base station, wherein the priority flag indicates that the UE is subscribed to a medical data monitoring service;
   in the LTE base station, verifying that the UE is authorized for enhanced quality of service for the medical data monitoring service;
   in the UE, sensing medical data associated with a user of the UE, and transferring the medical data for delivery to the LTE base station;
   in the LTE base station:
      receiving the medical data transmitted from the UE;
      determining if the medical data exceeds a predetermined threshold value; and
      when the medical data exceeds the predetermined threshold value, implementing the enhanced quality of service for the UE by increasing a power of a communication channel provided to the UE using beamforming.

2. The method of claim 1 wherein sensing the medical data associated with the user of the UE comprises sensing electrical heart activity of the user to generate electrocardiogram data.

3. The method of claim 1 wherein transferring the medical data for delivery to the LTE base station comprises transferring the medical data over a prioritized data bearer channel.

4. The method of claim 1 wherein verifying that the UE is authorized for the enhanced quality of service for the medical data monitoring service comprises receiving an indication that the UE is authorized for the enhanced quality of service for the medical data monitoring service from a home subscriber server (HSS) profile associated with the UE.

5. The method of claim 1 wherein implementing the enhanced quality of service for the UE by increasing the power of the communication channel provided to the UE using beamforming comprises establishing a beamformed communication link with the UE.

6. The method of claim 1 wherein implementing the enhanced quality of service for the UE comprises selecting a multiple-input multiple-output (MIMO) mode for the UE optimized for redundancy.

7. The method of claim 1 wherein implementing the enhanced quality of service for the UE comprises applying priority scheduling for quality of service class identifier (QCI)-five traffic associated with the UE.

8. A computer apparatus to operate a long term evolution (LTE) base station to facilitate increased quality of service in consideration of medical information, the apparatus comprising:
software instructions configured, when executed by the LTE base station, to direct the LTE base station to receive a radio resource control (RRC) message comprising a priority flag transmitted from a user equipment (UE), wherein the priority flag indicates that the UE is subscribed to a medical data monitoring service, verify that the UE is authorized for enhanced quality of service for the medical data monitoring service, receive medical data transmitted from the UE, wherein the UE senses the medical data from a user of the UE, determine if the medical data exceeds a predetermined threshold value, and when the medical data exceeds the predetermined threshold value, implement the enhanced quality of service for the UE by increasing a power of a communication channel provided to the UE using beamforming; and
at least one non-transitory computer-readable storage medium storing the software instructions.

9. The apparatus of claim 8 wherein the UE senses the medical data from the user of the UE by sensing electrical heart activity of the user to generate electrocardiogram data.

10. The apparatus of claim 8 wherein the software instructions configured to direct the LTE base station to receive the medical data transmitted from the UE comprises the software instructions configured to direct the LTE base station to receive the medical data over a prioritized data bearer channel.

11. The apparatus of claim 8 wherein the software instructions configured to direct the LTE base station to verify that the UE is authorized for the enhanced quality of service for the medical data monitoring service comprises the software instructions configured to direct the LTE base station to receive an indication that the UE is authorized for the enhanced quality of service for the medical data monitoring service from a home subscriber server (HSS) profile associated with the UE.

12. The apparatus of claim 8 wherein the software instructions configured to direct the LTE base station to implement the enhanced quality of service for the UE by increasing the power of the communication channel provided to the UE using beamforming comprises the software instructions configured to direct the LTE base station to establish a beamformed communication link with the UE.

13. The apparatus of claim 8 wherein the software instructions configured to direct the LTE base station to implement the enhanced quality of service for the UE comprises the software instructions configured to direct the LTE base station to select a multiple-input multiple-output (MIMO) mode for the UE optimized for redundancy.

14. The apparatus of claim 8 wherein the software instructions configured to direct the LTE base station to implement the enhanced quality of service for the UE comprises the software instructions configured to direct the LTE base station to apply priority scheduling for quality of service class identifier (QCI)-five traffic associated with the UE.

15. A long term evolution (LTE) base station to facilitate increased quality of service in consideration of medical information, the LTE base station comprising:
a wireless communication transceiver configured to receive a radio resource control (RRC) message comprising a priority flag transmitted from a user equipment (UE), wherein the priority flag indicates that the UE is subscribed to a medical data monitoring service; and
a processing system configured to verify that the UE is authorized for enhanced quality of service for the medical data monitoring service;
the wireless communication transceiver configured to receive medical data transmitted from the UE, wherein the UE senses the medical data from a user of the UE; and
the processing system configured to determine if the medical data exceeds a predetermined threshold value, and when the medical data exceeds the predetermined threshold value, and when the medical data exceeds the predetermined threshold value, implement the enhanced quality of service for the UE by increasing a power of a communication channel provided to the UE using beamforming.

16. The LTE base station of claim 15 wherein the UE senses the medical data from the user of the UE by sensing electrical heart activity of the user to generate electrocardiogram data.

17. The LTE base station of claim 15 wherein the wireless communication transceiver configured to receive the medical data transmitted from the UE comprises the wireless communication transceiver configured to receive the medical data over a prioritized data bearer channel.

18. The LTE base station of claim 15 wherein the processing system configured to implement the enhanced quality of service for the UE by increasing the power of the communication channel provided to the UE using beamforming comprises the processing system configured to establish a beamformed communication link with the UE.

19. The LTE base station of claim 15 wherein the processing system configured to implement the enhanced quality of service for the UE comprises the processing system configured to select a multiple-input multiple-output (MIMO) mode for the UE optimized for redundancy.

20. The LTE base station of claim 15 wherein the processing system configured to implement the enhanced quality of service for the UE comprises the processing system configured to apply priority scheduling for quality of service class identifier (QCI)-five traffic associated with the UE.

* * * * *